(12) United States Patent
Araki et al.

(10) Patent No.: US 8,258,103 B2
(45) Date of Patent: Sep. 4, 2012

(54) PESTICIDAL COMPOSITION

(75) Inventors: Tsutomu Araki, Fukuchiyama (JP); Naoki Sato, Yachiyo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 182 days.

(21) Appl. No.: 12/668,625

(22) PCT Filed: Jul. 11, 2008

(86) PCT No.: PCT/JP2008/062591
§ 371 (c)(1), (2), (4) Date: Jan. 11, 2010

(87) PCT Pub. No.: WO2009/008506
PCT Pub. Date: Jan. 15, 2009

(65) Prior Publication Data
US 2010/0184713 A1    Jul. 22, 2010

(30) Foreign Application Priority Data

Jul. 12, 2007 (JP) .................................. 2007-182986
May 20, 2008 (JP) .................................. 2008-131607

(51) Int. Cl.
*A61K 31/70* (2006.01)

(52) U.S. Cl. ........................................................ 514/28
(58) Field of Classification Search ............. 514/28
See application file for complete search history.

(56) References Cited

U.S. PATENT DOCUMENTS

| 5,202,242 A | 4/1993 | Mynderse et al. |
| 5,922,880 A | 7/1999 | Sakamoto et al. |
| 2006/0128642 A1 | 6/2006 | Malsam et al. |

FOREIGN PATENT DOCUMENTS

| JP | 6-506477 A | 7/1994 |
| JP | 9-151172 A | 6/1997 |
| JP | 11-506117 A | 6/1999 |
| JP | 2006-50961 A | 2/2006 |
| JP | 2006-517538 A | 7/2006 |
| WO | WO-97/00265 A1 | 1/1997 |

OTHER PUBLICATIONS

"Insecticidal combinations containing alkoxylated amines" Research Disclosure, Jan. 2006, No. 501, pp. 18-19, Disclosed Anonymously.
International Preliminary Report on Patentability (Form PCT/IB/373) and Written Opinion of the International Searching Authority (Form PCT/ISA/237) issued in PCT/JP2008/062591 (dated Feb. 9, 2010).

*Primary Examiner* — Elli Peselev
(74) *Attorney, Agent, or Firm* — Birch, Stewart, Kolasch & Birch, LLP

(57) ABSTRACT

The present invention provides a pesticidal composition comprising a compound represented by the formula (I):

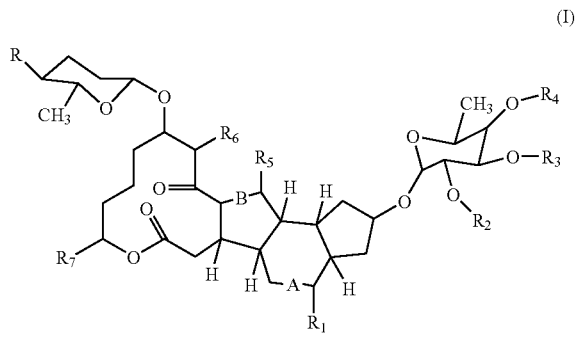

wherein A, B, R, $R_1$, $R_2$, $R_3$, $R_4$, $R_5$, $R_6$ and $R_7$ are as defined in the description, and 2,6-dichloro-4-(3,3-dichloroallyloxy) phenyl 3-[5-(trifluoromethyl)-2-pyridyloxy]propyl ether as active ingredients, and also provides a pest control method which comprises the step of applying an effective amount of the compound represented by the above formula (I) and an effective amount of 2,6-dichloro-4-(3,3-dichloroallyloxy) phenyl 3-[5-(trifluoromethyl)-2-pyridyloxy]propyl ether to pests or a place where pests inhabit.

4 Claims, No Drawings

PESTICIDAL COMPOSITION

TECHNICAL FIELD

The present invention relates to a pesticidal composition and so on.

BACKGROUND ART

Hitherto, various pesticidal compositions for controlling pests have been developed and used practically (see Patent Documents 1 to 3). However, conventional pesticidal compositions do not exert a satisfactory controlling effect in some cases, and therefore, there is still a need for development of a pesticidal composition having an excellent controlling effect.
Patent Document 1: WO 97/00265
Patent Document 2: JP-A 9-151172
Patent Document 3: WO 93/09126

DISCLOSURE OF THE INVENTION

Problems to be Solved by the Invention

An object of the present invention is to provide a pesticidal composition having an excellent controlling effect against pests.

Means for Solving the Problems

The present inventors found that a pesticidal composition comprising a compound represented by the following formula (I) and 2,6-dichloro-4-(3,3-dichloroallyloxy)phenyl 3-[5-(trifluoromethyl)-2-pyridyloxy]propyl ether as active ingredients could exert a greater effect in pest control as compared with a single application of each compounds, and thus the present invention was completed.

Effect of the Invention

According to the present invention, a pesticidal composition having an excellent controlling effect against pests and so on are provided.

BEST MODE FOR CARRYING OUT THE INVENTION

The present invention provides:
(1) A pesticidal composition comprising a compound represented by the formula (I):

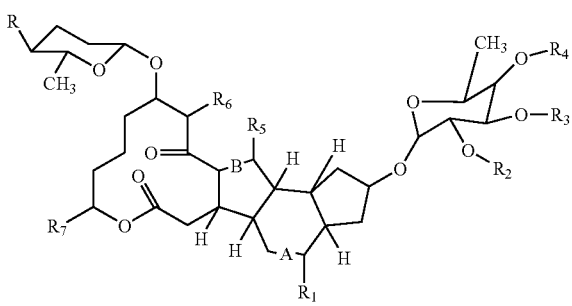

wherein A and B independently represent a single bond, a double bond or an ether linkage, R represents a group represented by the formula (II):

(wherein $R_8$ and $R_9$ independently represent a C1-C4 alkyl group, a C1-C4 haloalkyl group, a C1-C4 alkanoyl group or a protected amino group), or a group represented by the formula (III):

(wherein $R_{10}$ represents a C1-C4 alkyl group, a C1-C4 haloalkyl group, a C1-C4 alkanoyl group or a protected amino group), $R_1$ represents a hydrogen atom or a methyl group, $R_2$, $R_3$ and $R_4$ independently represent a C1-C4 alkyl group, a C1-C4 haloalkyl group, a C1-C4 alkanoyl group or a protected hydroxyl group, $R_5$ represents a hydrogen atom, a C1-C4 alkyl group, a C1-C4 alkylamino group or an alkylhydroxylamino group represented by the formula (IV):

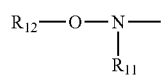

(wherein $R_{11}$ and $R_{12}$ independently represent a hydrogen atom, a C1-C4 alkyl group or a C1-C5 alkanoyl group), $R_6$ represents a hydrogen atom or methyl group, and $R_7$ represents a methyl group or an ethyl group; and 2,6-dichloro-4-(3,3-dichloroallyloxy)phenyl 3-[5-(trifluoromethyl)-2-pyridyloxy]propyl ether as active ingredients;

(2) The composition according to the above (1), wherein A is a single bond or a double bond, B is a double bond, R is a group represented by the formula (II):

(wherein $R_8$ and $R_9$ are methyl groups), $R_2$ is a methyl group, $R_3$ is a methyl group or an ethyl group, $R_4$ is a methyl group, $R_5$ is a hydrogen atom, $R_6$ is a methyl group, and $R_7$ is an ethyl group;

(3) The composition according to the above (2), wherein $R_3$ is an ethyl group;

(4) The composition according to the above (1), wherein the compound represented by the formula (I) is spinetoram;

(5) A pest control method which comprises a step of applying an effective amount of a compound represented by the formula (I):

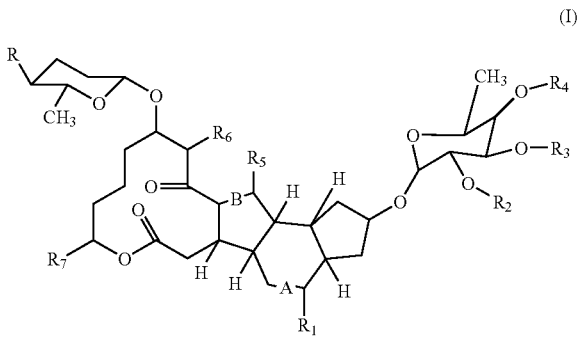

wherein A and B independently represent a single bond, a double bond or an ether linkage, R represents a group represented by the formula (II):

(wherein $R_8$ and $R_9$ independently represent a C1-C4 alkyl group, a C1-C4 haloalkyl group, a C1-C4 alkanoyl group or a protected amino group), or a group represented by the formula (III):

(wherein $R_{10}$ represents a C1-C4 alkyl group, a C1-C4 haloalkyl group, a C1-C4 alkanoyl group or a protected amino group), $R_1$ represents a hydrogen atom or a methyl group, $R_2$, $R_3$ and $R_4$ independently represent a C1-C4 alkyl group, a C1-C4 haloalkyl group, a C1-C4 alkanoyl group or a protected hydroxyl group, $R_5$ represents a hydrogen atom, a C1-C4 alkyl group, a C1-C4 alkylamino group or an alkylhydroxylamino group represented by the formula (IV):

(wherein $R_{11}$ and $R_{12}$ independently represent a hydrogen atom, a C1-C4 alkyl group or a C1-C5 alkanoyl group), $R_6$ represents a hydrogen atom or methyl group, and $R_7$ represents a methyl group or an ethyl group; and an effective amount of 2,6-dichloro-4-(3,3-dichloroallyloxy)phenyl 3-[5-(trifluoromethyl)-2-pyridyloxy]propyl ether to pests or a place where pests inhabit; and so on.

The compound represented by the above formula (I) may be referred to as "the present compound 1", and 2,6-dichloro-4-(3,3-dichloroallyloxy)phenyl 3-[5-(trifluoromethyl)-2-pyridyloxy]propyl ether may be referred to as "the present compound 2". The present compound 1 and the present compound 2 may be collectively referred to as "the present active ingredients". The composition having characteristics described in the above (1) may be referred to as "the composition of the present invention".

The present compound 1 is disclosed in WO 97/00265. The present compound 2 (generic name: pyridalyl) is disclosed in JP-A 9-151172.

For the present compound 1, the "C1-C4 alkyl group" means an alkyl group of 1 to 4 carbon atoms, and examples thereof include methyl, ethyl, propyl, isopropyl, butyl, isobutyl, sec-butyl and tert-butyl.

The "C1-C4 haloalkyl group" means an alkyl group of 1 to 4 carbon atoms which is substituted with at least one halogen atom (e.g., fluorine, chlorine, bromine or iodine), and examples thereof include chloromethyl, difluoromethyl, trichloromethyl, trifluoromethyl, 2-bromoethyl, 2,2,2-trifluoroethyl, 1,1,2,2,2-pentafluoroethyl, 3,3,3-trifluoropropyl and 4,4,4-trifluorobutyl.

The "C1-C4 alkanoyl group" means an alkanoyl group of 1 to 4 carbon atoms, and examples thereof include formyl, acetyl, 2-methylacetyl, 2,2-dimethylacetyl, propionyl, butyryl and isobutyryl.

The "protected hydroxyl group" means a hydroxyl group protected with a protecting group, and examples of the protecting group include those described in "Protective Groups in Organic Synthesis", T. W. Greene and P. G. M. Wuts, ed. 3, John Wiley & Sons, New York, 1999 and references cited therein.

The "protected amino group" means an amino group protected with a protecting group, and examples of the protecting group include those described in the above "Protective Groups in Organic Synthesis" and references cited therein.

The "C1-C4 alkylamino group" means an alkylamino group of 1 to 4 carbon atoms, and examples thereof include methylamino, ethylamino, propylamino, isopropylamino, butylamino, isobutylamino, sec-butylamino and tert-butylamino.

The "C1-C5 alkanoyl group" means an alkanoyl group of 1 to 5 carbon atoms, and examples thereof include formyl, acetyl, 2-methylacetyl, 2,2-dimethylacetyl, propionyl, butyryl, isobutyryl, pentanoyl and 2,2-dimethylpropionyl.

The present compound 1 may be present as an isomer including a tautomer and a stereoisomer based on an asymmetric carbon atom and a double bond (optical isomer, geometric isomer, etc.). In the present invention, the compound represented by the formula (I) includes all of these isomers and mixtures thereof.

The present compound 1 may be:

(1) a mixture of a compound represented by the formula (Ia):

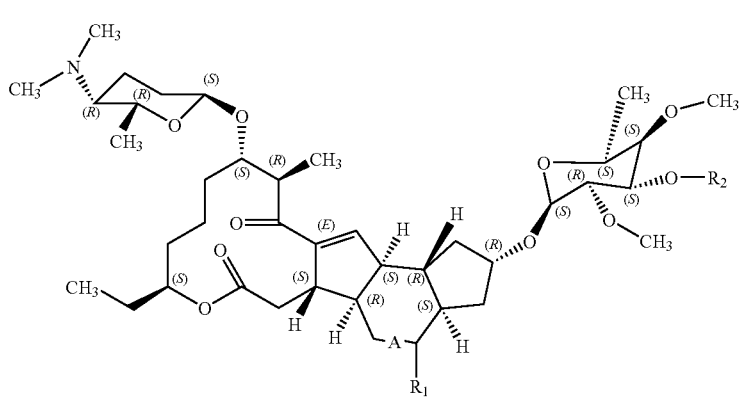

wherein A is a double bond, $R_1$ is a hydrogen atom and $R_2$ is a methyl group (hereinafter, referred to as "the compound A1a"), and a compound represented by the above formula (Ia) wherein A is a double bond, $R_1$ is a methyl group and $R_2$ is a methyl group (hereinafter, referred to as "the compound A1b"), or (2) a mixture of a compound represented by the above formula (Ia) wherein A is a single bond, $R_1$ is a hydrogen atom and $R_2$ is an ethyl group (hereinafter, referred to as "the compound B1a"), and a compound represented by the above formula (Ia) wherein A is a double bond, $R_1$ is a methyl group and $R_2$ is an ethyl group (hereinafter, described as "the compound B1b").

Particularly, the mixture (1) of the compound A1a and the compound A1b is known as the generic name of spinosad. The mixture (2) of the compound B1a and the compound B1b is known as the generic name of spinetoram.

The composition of the present invention may be in the form of a composition consisting of only the present active ingredients, or may be in the form of a formulation prepared by combining the present active ingredients with other ingredients, such as a liquid formulation, e.g. an oil solution, an emulsifiable concentrate, a flowable formulation and an aerosol formulation, a solid formulation, e.g. a wettable powder, a resin formulation, a granule, a dust, a poison bait and a microcapsule formulation, a smoking formulation, a fumigant, an ULV formulation, a spot-on formulation, or a shampoo formulation. Hereinafter, a formulation containing the present active ingredients may be referred to as "the present formulation".

The present formulation is prepared by a general method which comprises supporting, dissolving or dispersing the present active ingredients on/in a carrier appropriately selected from carriers including a solid carrier, a liquid carrier and a gaseous carrier depending on the form of the formulation, and adding some pharmaceutical additives as needed.

The present formulation contains usually 0.01 to 90% by weight, preferably 0.1 to 80% by weight of the present active ingredients.

The weight ratio of the present compound 1 to the present compound 2 in the present active ingredients is from 100:1 to 1:100, preferably from 10:1 to 1:10.

Examples of the solid carrier that may be contained in the present formulation include finely-divided powder and granules of clay (kaolin clay, diatomaceous earth, synthetic hydrated silicon oxide, bentonite, agalmatolite clay, acid clay, talc, etc.), ceramics, other inorganic minerals (sericite, quartz, sulfur, calcium carbonate, hydrated silica, etc.), activated carbon, and chemical fertilizers (ammonium sulfate, ammonium phosphate, ammonium nitrate, urea, ammonium chloride, etc.).

Examples of the liquid carrier include water, alcohols (methanol, ethanol, etc.), ketones (acetone, methyl ethyl ketone, etc.), aromatic hydrocarbons (benzene, toluene, xylene, ethylbenzene, methylnaphthalene, etc.), aliphatic hydrocarbons (hexane, kerosene, light oil, etc.), alicyclic hydrocarbons (cyclohexane, etc.), esters (ethyl acetate, butyl acetate, etc.), nitriles (acetonitrile, isobutyronitrile, etc.), ethers (diisopropyl ether, dioxane, etc.), acid amides (N,N-dimethylformamide, N,N-dimethylacetamide, etc.), halogenated hydrocarbons (dichloromethane, trichloromethane, carbon tetrachloride, etc.), dimethyl sulfoxide, and vegetable oils (soybean oil, cotton seed oil, etc.).

Examples of the gaseous carrier include fluorocarbon, butane gas, LPG (liquefied petroleum gas), dimethyl ether, and carbon dioxide gas.

Examples of the pharmaceutical additive that may be contained in the present formulation include a surfactant, a binder, a dispersant, a thickener, a stabilizer, an antioxidant, a propellant, a defoaming agent, a rust preventive, an antifreezing agent, a dye, and a pigment. Examples of the surfactant include alkyl sulfate salts, alkyl sulfonate salts, alkylaryl sulfonate salts, alkyl aryl ethers and their polyoxyethylenated derivatives, polyethylene glycol ethers, polyhydric alcohol esters, and sugar alcohol derivatives.

Other examples of the pharmaceutical additive include casein, gelatin, polysaccharides (starch, gum arabic, cellulose derivatives, alginic acid, etc.), lignin derivatives, bentonite, saccharides, synthetic water-soluble polymers (polyvinyl alcohol, polyvinyl pyrrolidone, polyacrylic acid, etc.), PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), fatty acids, and fatty acid esters.

The present formulation contains usually 0.001 to 50% by weight, preferably 0.01 to 30% by weight of the pharmaceutical additive.

The aerosol formulation is prepared, for example, by charging a container having a jet system, such as a spray can, with a formulation containing the present active ingredients in the form of an oil solution, an emulsifiable concentrate, a flowable formulation or the like together with a propellant.

The poison bait is prepared by mixing a base material, the present active ingredients and other ingredients.

Examples of the base material for the poison bait include a food ingredient such as cereal powder, vegetable oil, sugar and crystalline cellulose, an antioxidant such as dibutylhydroxytoluene and nordihydroguaiaretic acid, a preservative such as dehydroacetic acid, an agent for preventing children and pets from eating the poison bait by mistake such as hot pepper powder, a pest-attractive perfume such as cheese perfume, onion perfume and peanut oil.

The present formulation is applied to a plant or soil where pests inhabit by such a method that the present active ingredients can be provided in an amount effective for pest control. In the case of the present formulation in the form of a wettable powder, an emulsifiable concentrate, a flowable formulation, an aerosol formulation or a dust, examples of an application method include spraying of the present formulation or, if needed, a dilution thereof with water or an organic solvent on the leaves and stems of a plant where pests inhabit; spraying of the present formulation or a dilution thereof on soil near a plant where pests inhabit or soil where pests inhabit; and drenching of soil near a plant where pests inhabit or soil where pests inhabit with the present formulation or a dilution thereof. In the case of the present formulation in the form of a poison bait or a granule, examples of an application method include sprinkling of the present formulation on soil near a plant where pests inhabit or soil where pests inhabit; and drenching of soil near a plant where pests inhabit or soil where pests inhabit with the present formulation.

Examples of an organic solvent used for dilution of the oil solution include mineral oils (naphthalene, kerosene, diesel oil, etc.) and vegetable oils (soybean oil, cottonseed oil, etc.).

Examples of a place where agricultural pests inhabit to be controlled according to the present invention include the foliage, flowers, buds and roots of plants such as farm crops; the soil and waterside near plants; forests, rangelands, grasslands, houses, and barns.

The pest control method of the present invention comprises the step of applying an effective amount of the present active ingredients to pests or a place where pests inhabit (a plant body, soil, the inside of a house, an animal body, etc.). The present compound 1 and the compound 2, which are the present active ingredients, may be applied separately, or a mixture of the present compound 1 and the compound 2 may be applied.

Examples of a method of applying the present active ingredients include spray treatment with a liquid formulation, drenching treatment with a liquid formulation, spray treatment with a dust, spray treatment with a granule, soil incorporation treatment with a granule, seed treatment, water culture medium treatment, fumigation treatment, and transpiration treatment.

The spray treatment with a liquid formulation is a treatment method comprising spraying a dilution of the active ingredient with water or various solvents on a pest itself, the surface of a plant, or the soil or waterside near a plant. Specific examples thereof include foliage spray treatment, flower cluster spray treatment, trunk spray treatment, treatment under tree crowns or around trunks, soil spray treatment, water surface spray treatment, spray treatment by using a manned helicopter, spray treatment by using an unmanned helicopter, and spray treatment by using an aircraft.

The drenching treatment with a liquid formulation is a treatment method comprising applying the active ingredient to soil, an irrigation water or the surface or vessels of a plant, for the purpose of allowing the active ingredient to permeate and transfer into the interior of the plant body of a crop to be protected from damage such as ingestion by pests. Specific examples thereof include drenching treatment of plant foot soil, drenching treatment of planting furrow soil, drenching treatment of planting row soil, overall soil drenching treatment, chemical injection treatment into the vessels of a plant, chemical drip irrigation treatment, chemigation treatment, drenching treatment of a seedling raising box, drenching treatment of a nursery bed, and root immersion treatment.

The spray treatment with a granule or the soil incorporation treatment with a granule is a treatment method comprising applying a granule containing the active ingredient to the soil or waterside near a plant, for the purpose of allowing the active ingredient to permeate and transfer into the interior of the plant body of a crop to be protected from damage such as ingestion by pests through the root part, surface or the like of the plant. Specific examples thereof include planting hole spray treatment, planting hole soil incorporation treatment, plant foot spray treatment, plant foot soil incorporation treatment, planting furrow spray treatment, planting furrow soil incorporation treatment, planting row spray treatment, planting row soil incorporation treatment, seedling raising tray spray treatment, bed soil incorporation treatment, cover soil/ridge soil incorporation treatment, overall soil spray treatment, overall soil incorporation treatment, water surface spray treatment, foliar spray treatment in a growing period and flower cluster spray treatment.

The spray treatment with a granule or the soil incorporation treatment with a granule is a treatment method comprising applying a granule containing the active ingredient to the soil or waterside near a plant, for the purpose of allowing the active ingredient to permeate and transfer into the interior of the plant body of a crop to be protected from damage such as ingestion by pests through the root part, surface or the like of the plant. Specific examples thereof include planting hole spray treatment, planting hole soil incorporation treatment, plant foot spray treatment, plant foot soil incorporation treatment, planting furrow spray treatment, planting furrow soil incorporation treatment, planting row spray treatment, planting row soil incorporation treatment, seedling raising tray spray treatment, bed soil incorporation treatment, cover soil/ridge soil incorporation treatment, overall soil spray treatment, overall soil incorporation treatment, water surface spray treatment, foliar spray treatment in a growing period, flower cluster spray treatment, and water surface spray treatment.

The seed treatment is a treatment method comprising applying the active ingredient directly to or around the seed, seed tuber or bulb of a crop to be protected from damage such as ingestion by pests. Specific examples thereof include spray treatment, spray coating treatment, immersion treatment, impregnation treatment, film coating treatment, and pellet coating treatment.

The water culture medium treatment is a treating method comprising adding the active ingredient to a water culture medium or the like, for the purpose of allowing the active ingredient to permeate and transfer into the interior of the plant body of a crop to be protected from damage such as ingestion by pests through the root part or the like of the plant. Specific examples thereof include incorporation into a water culture medium.

The fumigation treatment or the transpiration treatment is a treatment method comprising diffusing the active ingredient from a liquid formulation or a carrier containing the active ingredient into the air by means of burning of an exothermic agent or an auxiliary smoking agent, an external heat source utilizing chemical reaction, electricity or the like, or a natural diffusion, thereby the active ingredient is allowed to adhere to the plant surface or a pest itself. Specific examples thereof include treatment with a fumigant, treatment with a heating transpiration agent, and treatment with a resin transpiration agent.

According to the pest control method of the present invention, the present active ingredients may control pests in cultivated lands and the like where plants including "crops" listed below are grown, without causing chemical damage to the "crops".

The "crops" include plants listed below.

Agricultural crops: maize, rice, wheat, barley, rye, oat, sorghum, cotton, soybean, peanut, buckwheat, beet, rapeseed, sunflower, sugarcane, tobacco, etc.;

Vegetables: solanaceous vegetables (egg plant, tomato, green pepper, hot pepper, potato, etc.), cucurbitaceous vegetables (cucumber, pumpkin, zucchini, water melon, melon, etc.), brassicaceous vegetables (Japanese radish, turnip, horseradish, kohlrabi, Chinese cabbage, cabbage, brown mustard, broccoli, cauliflower, etc.), asteraceous vegetables (burdock, garland chrysanthemum, artichoke, lettuce, etc.), liliaceous vegetables (scallion, onion, garlic, asparagus, etc.), umbelliferous vegetables (carrot, parsley, celery, parsnip, etc.), chenopodiaceous vegetables (spinach, chard, etc.), lamiaceous vegetables (Japanese basil, mint, basil, etc.), strawberry, sweet potato, yam, aroid etc.;

Flowers and ornamental plants: *acanthus*, morning glory, *azalea, hydrangea, anemone raddeana, rhodohypoxis baurii, anemone, polygonatum odoratum, amaryllis, iris, alyssum, armeria, arctotis*, China aster, edible flower, *Bauera ruibioides*, Cuban lily, *Hosta montana*, Mexican aster, four o'clock, *Hypericum*, oriental poppy, *gentiana makinoi, Hosta aureomarginata*, Japanese iris, *clematis patens, gazania, Casa Blanca*, carnation, showy lily, *gerbera, kalanchoe, calceolaria*, curry plant, Carolina jasmine, canna, *chrysanthemum, Brugmansia*, yellow cosmos, plantain lily, KimJongilia, tea tree (*Manuka*), pot marigold, myrtle, *nasturtium, gladiolus*, Siam tulip, clematis, cockscomb, shrimp plant, midday flower, cosmos, *Hosta sieboldii, Convolvulus arvensis, Hosta sagae*, primrose, saffron crocus, *salvia*, cyclamen, moss phlox, *Paeonia lactiflora, Anemone hupehensis, Bletilla striata*, sweet pea, lily of the valley, snowflake, *portulaca*, violet, rose of Sharon, yarrow, Chinese pink, *zephyranthes, pelargonium*, geum, zepher lily, *dahlia, tithonia*, tulip, chocolate cosmos, *Vinca major, scilla*, downy myrtle, German iris, passionflower, *dianthus*, rape blossom, Madagascar periwinkle, soft windflower, *nemophila*, Nerine, swamp chrysanthemum (North pole), Japanese water iris (*iris ensata* var. *spontanea*), *verbena, hibiscus*, Joseph's coat, coral flower, Japanese water iris (*Iris ensata*), eastern redbud, spring star-flower, wavyleaf sea-lavender, California poppy, pansy, Virginia stock, daisy, corn poppy, Himalayan creeping saxifrage, sunflower, hyacinth, crape-myrtle, *Geranium, fuchsia, freesia, primula*, garden balsam, ground-cherry, peony, *Tricyrtis*, marguerite, marigold, *Gymnaster savatieri*, strawflower, muscari, Japanese kerria, lily, *ranunculus, lantana, gentian, Lupinus, lobelia*, etc.;

Ornamental foliage plants: ivy, cattail, *aglaonema, adiantum, asparagus, asplenium, ananas, aphelandra, alocasia, anthurium*, Indian rubber tree, *nepenthes, aechmea, aeschynanthus, episcia, strelitzia augusta*, spiders plant, Chinese banyan, kapok, *caladium, calathea*, velvet plant (*Gynura*), *Guzumania, Ctenanthe*, gum tree, *crassula, croton, Alocasia odora*, orange jessamine, coffee tree, *massangeana*, conifers, *coleus*, cordyline, *columnea, sansevieria*, Chinese ixora, *schefflera, cissus, cyperus*, reed rhapis, silk jessamine, *syngonium, strelitzia, spathiphyllum, senecio, zebrina*, Japanese sago palm, *tillandsia, tupidanthus*, coral tree, *dizygotheca, dieffenbachia, duranta*, bottle palm, *dracaena, tradescantia, neoregelia, nephrolepis*, hearts vine, *hibiscus, pachypodium*, Guiana chestnut (*Pachira*), ponytail, staghorn fern, *pilea, fatshedera, ficus pumila, philodendron, bougainvillea, phoenix, fittonia, pteris*, bridal veil, *vriesea, plectranthus, begonia, peperomia, heliconia, benjamina, poinsettia, pothos, hoya, maranta*, Belgian evergreen, milkbush, oyster plant, *monstera*, palm, yucca, *lantana*, etc.;

Fruits: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruit, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut palm, etc.;

Trees other than fruit trees: tea, mulberry, flowering trees, street trees (ash tree, birch, dogwood, *eucalyptus, ginkgo*, lilac, maple tree, oak, poplar, cercis, liquidambar, *platanus*, zelkova, Japanese arborvitae, fir tree, Japanese hemlock, needle juniper, pine, spruce, yew), etc.

Fruits: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruit, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut palm, etc.;

Trees other than fruit trees: tea, mulberry, flowering trees, street trees (ash tree, birch, dogwood, eucalyptus, ginkgo, lilac, maple tree, oak, poplar, cercis, liquidambar, *platanus*, zelkova, Japanese arborvitae, fir tree, Japanese hemlock, needle juniper, pine, spruce, yew), etc.

The above-described "crops" include crop plants which have become resistant to an HPPD inhibitor such as isoxaflutole, an ALS inhibitor such as imazethapyr or thifensulfuron-methyl, an EPSP synthesizing enzyme inhibitor, a glutamine synthesizing enzyme inhibitor, or an herbicide such as bromoxynil by a classical breeding method or a genetic engineering technique.

Examples of the "crops" having herbicidal resistance given by a classic breeding technique include Clearfield (registered trademark) canola which is resistant to imidazolinone herbicides such as imazethapyr, and STS soybean which is resistant to sulfonylurea ALS inhibitor herbicides such as tifensulfuron methyl.

Examples of the "crops" having herbicidal resistance given by a genetic engineering technique include corn, soybean and cotton having resistance to glyphosate or glufosinate, which are already on the market under the product names of Roundup Ready (registered trademark), Liberty Link (registered trademark), etc.

The "crops" include crop plants which have acquired ability to produce insecticidal toxins known as selective toxins produced from *Bacillus* bacteria by a genetic engineering technique.

Examples of insecticidal toxins expressed in such genetically engineered plants include insecticidal proteins produced from *Bacillus cereus* or *Bacillus popilliae*; δ-endotoxins such as Cry1Ab, Cry1Ac, Cry1F, Cry1Fa2, Cry2Ab, Cry3A, Cry3Bb1 and Cry9C produced from *Bacillus thuringiensis*; insecticidal proteins such as VIP1, VIP2, VIP3 and VIP3A; insecticidal proteins produced from nematode; toxins produced by animals such as a scorpion toxin, a spider toxin, a bee toxin and an insect specific nervous system toxin; filamentous fungus toxins; plant lectins; agglutinins; protease inhibitors such as trypsin inhibitors, serine protease inhibitors, patatin, cystatin and papain inhibitors; ribosome inactivation proteins (RIP) such as ricins, corn-RIP, abrins, luffin, saporins, and bryodin; steroid metabolism enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel and calcium channel inhibitors; Juvenile hormone esterase; diuretic hormone receptors; stilbene synthase; bibenzyl synthase; chitinase; and glucanases.

Further examples of insecticidal toxins expressed in such genetically engineered plants include hybrid toxins of δ-endotoxin such as Cry1Ab, Cry1Ac, Cry1F, Cry1Fa2, Cry2Ab, Cry3A, Cry3Bb1 and Cry9C, and insecticidal proteins such as VIP1, VIP2, VIP3 and VIP3A, and insecticidal proteins in which a part of amino acids constituting the insecticidal proteins is deleted or modified. The hybrid toxins are created by combining different domains of the above insecticidal proteins by a genetic engineering technique.

An example of the toxin in which a part of amino acids constituting the insecticidal protein is deleted includes Cry1Ab in which a part of amino acids is deleted.

An example of the toxin in which a part of amino acids constituting the insecticidal protein is modified is made by substitution of one or more amino acids of a natural toxin.

Examples of the insecticidal toxins and genetically engineered crop plants which have the ability to produce the insecticidal toxins are described in EP-A-0374753, WO 93/07278, WO 95/34656, EP-A-0427529, EP-A-451878 and WO 03/052073.

Such genetically engineered plants have become resistant to attack by Coleopteran pests, Dipteran pests and/or Lepidopteran pests due to the toxins which the plants have.

Genetically engineered plants having one or more pest-resistant insecticidal genes and expressing one or more insecticidal toxins are already known, and some of them are commercially available.

Examples of the genetically engineered plants include YieldGard (registered trademark) (a corn variety expressing Cry1Ab toxin), YieldGard Rootworm (registered trademark) (a corn variety expressing Cry3Bb1 toxin), YieldGard Plus (registered trademark) (a corn variety expressing Cry1Ab and Cry3Bb1 toxins), Herculex I (registered trademark) (a corn variety expressing Cry1Fa2 toxin and phosphinothricin N-acetyltransferase (PAT) to confer resistance to glufosinate), NuCOTN33B (registered trademark) (a cotton variety expressing Cry1Ac toxin), Bollgard I (registered trademark) (a cotton variety expressing Cry1Ac toxin), Bollgard II (registered trademark) (a cotton variety expressing Cry1Ac and Cry2Ab toxins), VIPCOT (registered trademark) (a cotton variety expressing VIP toxin), NewLeaf (registered trademark) (a potato variety expressing Cry3A toxin), NatureGard (registered trademark), Agrisure (registered trademark) GT Advantage (GA21 glyphosate-resistance character), Agrisure (registered trademark) CB Advantage (Btll corn borer (CB) character), and Protecta (registered trademark).

The "crops" also include crop plants which have acquired ability to produce selective anti-pathogen substances by a genetic engineering technique.

Examples of the anti-pathogen substances include PR proteins (PRPs, described in EP-A-0392225). Such anti-pathogen substances and genetically engineered plants capable of producing them are described, for example, in EP-A-0392225, WO 95/33818 and EP-A-0353191.

Examples of anti-pathogen substances expressed in such genetically engineered plants include ion channel inhibitors such as sodium channel inhibitors and calcium channel inhibitors (KP1, KP4 and KP6 toxins and the like produced by virus are known); stilbene synthase; bibenzyl synthase; chitinase; glucanase; PR proteins; microorganism-producing substances such as peptide antibiotics, antibiotics having a heterocycle, and protein factors relating to resistance against palant pathogens (described in WO 03/000,906).

According to the pest control method of the present invention, the present active ingredients may be used in combination with other pesticides such as insecticides, acaricides, nematocides, fungicides, herbicides, plant hormone agents and plant growth regulators, synergists, crop injury-reducing agents, pigments, fertilizers, soil conditioners, animal feed and the like.

The present active ingredients or the present active ingredients dissolved in a solvent can be also supported on a resin such as polypropylene or polyethylene by kneading, surface treatment, etc. to prepare a resin formulation. Such a resin formulation is applied to a habitat of pests by being placed near plants such as agricultural crop plants.

Examples of pests which can be controlled by the present invention include arthropods such as insects and mites, and nemathelminthes such as nematodes listed below.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper, and (*Nephotettix virescens*); aphids (Aphididae) such as cotton aphid (*Aphis gossypii*), green peach aphid (*Myzus persicae*), green citrus aphid (*Aphis citricola*), turnip aphid (*Lipaphis pserudobrassicae*), pear green aphid (*Nippolachnus piri*), black citrus aphid (*Toxoptera aurantii*), and tropical citrus aphid (*Toxoptera citricidus*); stink bugs (Pentatomidae) such as green stink bug (*Nezara antennata*), narrow coreidbug (*Cletus punctiger*), bean bug (*Riptortus clavetus*), and brownwinged green bug (*Plautia stali*); whiteflies (Aleyrodidae) such as greenhouse whitefly (*Trialeurodes vaporariorum*), and sweetpotato whitefly (*Bemisia tabaci*); scales (Coccidae) such as Calformia red scale (*Aonidiella aurantii*), San Jose scale (*Comstockaspis perniciosa*), citrus north scale (*Unaspis citri*), white peach scale (*Pseudaulacaspis pentagona*), olive scale (*Saissetia oleae*), purple scale (*Lepidosaphes beckii*), red wax scale (*Ceroplastes rubens*), and cottonycushion scale (*Icerya purchasi*); lace bugs (Tingidae); psyllids (Psyllidae); etc.

Lepidoptera:

Pyralid moths (Pyralidae) such as rice stem borer (*Chilo suppressalis*), rice leafroller (*Cnaphalocrocis medinalis*), European corn borer (*Ostrinia nubilalis*), cabbage webworm (*Hellula undalis*), bluegrass webworm (*Parapediasia teterrella*), cotton leafroller (*Notarcha derogata*), and Indian meal moth (*Plodia interpunctella*); owlet moths (Noctuidae) such as common cutworm (*Spodoptera litura*), armyworm (*Pseudaletia separata*), cabbage armyworm (*Mamestra brassicae*), black cutworm (Agrotis *Thoricoplusia* spp., *Heliothis* spp., and *Helicoverpa* spp. such as corn earworm (*Helicoverpa armigera*); white butterflies (Pieridae) such as common white (*Pieris rapae*); tortricid moths (Tortricidae) such as *Adoxophyes* spp. such as smaller tea tortrix (*Adoxophyes honmai*) and summer fruit tortrix (*Adoxophyes orana*), and oriental fruit moth *Grapholita molesta*), and codling moth (*Cydia pomonella*); Carposimidae such as peach fruit moth (*Carposina niponensis*); lyonetiid moths (Lyonetiidae) such as *Lyonetia prunifoliella*; tussock moths (Lymantriidae) such as *Lymantria* spp., and *Euproctis* spp.; yponomeutid moths (Yponomeutidae) such as diamondback moth (*Plutella xylostella*); gelechiid moths (Gelechiidae) such as pink bollworm (*Pectinophora gossypiella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*); etc.

Diptera:

Culices such as common mosquito (*Culex pipiens pallens*), and *Cluex tritaeniorhynchus*; *Aedes* spp. such as yellow fever mosquito (*Aedes aegypti*), and Asian tiger mosquito (*Aedes albopictus*); *Anopheles* spp. such as *Anopheles sinensis*; chironomids (Chironomidae); house flies (Muscidae) such as *Musca domestica*, and *Muscina stabulans*; blow flies (Calliphoridae); flesh flies (Sarcophagidae); little house flies (Fanniidae); anthomyiid flies (Anthomyiidae) such as seedcorn fly (*Delia platura*), and onion fly (*Delia antiqua*); leafminer flies (Agromyzidae) such as legume leafminer (*Liriomyza trifolii*); fruit flies (Tephritidae); Drosophilidae; moth flies (Psychodidae); Simuliidae; Tabanidae; stable flies, etc.

Hymenoptera:

Sawflies (Tenthredinidae) such as Cabbage sawfly (*Athalia rosae*); Argidae such as rose sawfly (*Arge pagana*); hornets (Vespidae) such as yellow hornet (*Vespa simillima*), and *Polistes chinensis*; ants (Formicidae) such as pharaoh ant (*Monomorium pharaosis*); bethylid wasps (Bethylidae), etc.

Coleoptera:

Corn root worms (*Diabrotica* spp.) such as Western corn root worm (*Diabrotica virgifera virgifera*), and Sourthern corn root worm (*Diabrotica undecimpunctata* howardi); scarabs (Scarabaeidae) such as cupreous chafer (*Anomala cuprea*), and soybean beetle (*Anomala rufocuprea*); weevils such as maize weevil (*Sitophilus zeamais*), rice water weevil (*Lissorhoptrus oryzophilus*), alfalfa weevil (*Hypera pastica*), and azuki bean weevil (*Callosobruchus chinensis*); darkling beetles (Tenebrionidae) such as yellow mealworm (*Tenebrio molitor*), and red flour beetle (*Tribolium castaneum*); leaf beetles (Chrysomelidae) such as cucurbit leaf beetle (*Aulacophora femoralis*), striped flea beetle (*Phyllotreta striolata*), and Colorado potato beetle (*Leptinotarsa decemlineata*); *Epilachna* such as Twenty-eight-spotted ladybird (*Epilachna vigintioctopunctata*); false powderpost beetles (Bostrychidae); bark beetles (Scolytidae) such as powder post beetle (*Lyctus brunneus*); longhorn beetles (Cerambycidae); *Paederus fuscipens*, etc.

Blattodea:

German cockroach (*Blattella germanica*), smokybrown cockroach (*Periplaneta fuliginosa*), American cockroach (*Periplaneta americana*), *Periplaneta brunnea*, oriental cockroach (*Blatta orientalis*), etc.

Thysanoptera:

Thrips (Thripidae) such as melon thrips (*Thrips palmi*), onion thrips (*Thrips tabaci*), banana flower thrips (*Thrips hawaiiensis*), yellow tea thrips (*Scirtothrips dorsalis*), flower thrips (*Frankliniella intonsa*), yellow citrus thrips (*Frankliniella occidentalis*), *Ponticulothrips diospyrosi*, etc.

Orthoptera:

Mole crickets, grasshoppers, etc.

Shiphonaptera:

Cat flea (*Ctenocephalides felis*), dog flea (*Ctenocephalides canis*), human flea (*Pulex irritans*), etc.

Anoplura:

Head louse (*Pediculus humanus humanus*), Human body louse (*Pediculus humanus corporis*), crab louse (*Phthirus pubis*), etc.

Termites such as Japanese subterranean termite (*Reticulitermes speratus*), Formosan subterranean termite (*Coptotermes formosanus*), western drywood termite (*Incisitermes minor*), Daikoku drywood termite (*Cryptotermes domesticus*), *Odontotermes formosanus*, *Neotermes koshunensis*, *Glyptotermes satsumesis*, *Glyptotermes nakajimai*, *Glyptotermes fuscus*, *Glyptotermes kodamai*, *Glyptotermes kushimensis*, Japanese dampwood termite (*Hodotermopsis japonica*), *Coptotermes guangzhoensis*, *Reticulitermes miyatakei*, eastern subterranean termite (*Reticulitermes flavipes amamianus*), *Reticulitermes* sp., *Nasutitermes takasagoesis*, *Pericapritermes nitobei*, *Sinocapritermes mushae*, etc.

Isopoda:

Common rough wood louse (*Porcellio scaber*), *Porcellionides pruinosus*, common pill bug (*Armadillidium vulgare*), etc.

Chilopoda:

*Scolopendra subspinipes mutilans*, *Scolopendra subspinipes japonica*, House centipede (*Thereuonema hilgendorfi*), etc.

Diplopoda:

Garden millipede (*Oxidus gracilis*), *Parafontaria laminata laminata*, etc.

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as tomato rust mite (*Aculops lycopersici*), pink citrus rust mite (*Aculops pelekassi*), and purple tea mite (*Calacarus carinatus*); tarosonemid mites (Tarsonemidae) such as broad mite (*Polyphagotarsonemus latus*); false spider mites (Tenuipalpidae); Tuckerellidae; rat mites; ticks (Ixodidae); acarid mites (Acaridae); house dust mites (Pyroglyphidae) such as *Dermatophagoides farinae*; cheyletide mites (Cheyletidae) such as Chelacaropsis moorei; parasitoid mites (Dermanyssidae), etc.

Nematoda:

Root-lesion nematode such as coffee root-lesion nematode (*Pratylenchus coffeae*), *Pratylenchus fallax*, tea root-lesion nematode (*Pratylenchus loosi*), and walnut root-lesion nematode (*Pratylenchus vulnus*); cyst nematodes such as soybean cyst nematode (*Heterodera glycines*), and potato cyst nematode (*Globodera rostochiensis*); root-knot nematodes such as northern root-knot nematode (*Meloidogyne hapla*), and southern root-knot nematode (*Meloidogyne incognita*); *Aphelenchoides* sp. such as rice white-tip nematode (*Aphelenchoides besseyi*), and strawberry nematode (*Aphelenchoides fragariae*); stunt nematodes (*Tylenchorhynchus* sp.), ring nematodes (*Criconemoides* sp.), pin nematodes (*Paratylenchus* sp.), *Longidorus* sp., *Trichodorus* sp., etc.

When the composition of the present invention or the present active ingredient is used for pest control, the application amount thereof is such an amount that the present compound 1 and the present compound 2 are applied in a combined amount of usually 0.1 to 1,000 g, preferably 1 to 100 g per 10 ares. When the composition of the present invention is in the form of an emulsifiable concentrate or a flowable formulation, it is usually applied after it is diluted with water so that the active ingredient concentration becomes 1 to 500,000 ppm, preferably 10 to 100,000 ppm. When the composition of the present invention is in the form of a granule or a dust, it is usually used as it is. The composition of the present invention or the present active ingredient may be applied directly to pests or plants such as crop plants to be protected from pests, or may be applied to a place where pests inhabit, thereby the pests can be controlled.

The application amount and concentration vary depending on conditions such as the type of a formulation, an application period, an application area, an application method, the kind of a pest, the extent of damage and the like, and may be appropriately increased or decreased regardless of the above-described ranges.

Hereinafter, the present invention will be explained in more detail by the way of Formulation Examples and Test Examples which the present invention is not limited to.

First, Formulation Examples will be described. The term "part(s)" means part(s) by weight.

Formulation Example 1

5 parts of spinetoram as the present compound 1, 5 parts of pyridalyl as the present compound 2, 8 parts of polyoxyethylene styrylphenyl ether, 2 parts of calcium dodecylbenzenesulfonate and 80 parts of xylene are mixed uniformly to obtain an emulsifiable concentrate.

Formulation Example 2

4 parts of spinetoram as the present compound 1, 20 parts of pyridalyl as the present compound 2, 3 parts of sodium dodecylbenzenesulfonate, 3 parts of sodium ligninsulfonate and 70 parts of diatomaceous earth are mixed and milled uniformly with a jet air mill to obtain a wettable powder.

Formulation Example 3

0.5 part of spinetoram as the present compound 1, 1 part of pyridalyl as the present compound 2, 48.5 parts of talc and 50 parts of clay are mixed and stirred uniformly to obtain a dust.

Formulation Example 4

To 1 part of spinetoram as the present compound 1 and 4 parts of pyridalyl as the present compound 2 are added 5 parts of sodium dodecylbenzenesulfonate, 30 parts of bentonite and 60 parts of clay. The mixture is mixed and stirred thoroughly. Then, a proper amount of water is added to the mixture. The mixture is stirred, granulated with a granulator and then dried by ventilation to obtain a granule.

Formulation Example 5

5 parts of polyoxyethylene styrylphenyl ether sulfate, 20 parts of a 1% xanthan gum aqueous solution, 3 parts of a smectite mineral and 60 parts of water are mixed uniformly. To the mixture are added 2 parts of spinetoram as the present compound 1 and 10 parts of pyridalyl as the present compound 2. The mixture is stirred thoroughly and then wet-milled with a sand mill to obtain a flowable formulation.

Formulation Example 6

0.02 part of spinetoram as the present compound 1 and 0.1 part of pyridalyl as the present compound 2 are dissolved in 10 parts of acetone. The solution is uniformly mixed with 99.88 parts of a powdered solid animal feed (CE-2: powdered chow for breeding, manufactured by Clea Japan Inc.). Then, the mixture is air dried to remove acetone to obtain a poison bait.

Formulation Example 7

0.1 part of spinetoram as the present compound 1 and 0.1 part of pyridalyl as the present compound 2 are dissolved in 5 parts of xylene and 5 parts of trichloroethane. The solution is mixed with 89.8 parts deodorized kerosene to obtain an oil solution.

Formulation Example 8

5 parts of spinosad as the present compound 1, 5 parts of pyridalyl as the present compound 2, 8 parts of polyoxyethylene styrylphenyl ether, 2 parts of calcium dodecylbenzenesulfonate and 80 parts of xylene are mixed uniformly to obtain an emulsifiable concentrate.

Formulation Example 9

4 parts of spinosad as the present compound 1, 20 parts of pyridalyl as the present compound 2, 3 parts of sodium dodecylbenzenesulfonate, 3 parts of sodium ligninsulfonate and 70 parts of diatomaceous earth are mixed and milled uniformly with a jet air mill to obtain a wettable powder.

Formulation Example 10

0.5 part of spinosad as the present compound 1, 1 part of pyridalyl as the present compound 2, 48.5 parts of talc and 50 parts of clay are mixed and stirred uniformly to obtain a dust.

Formulation Example 11

To 1 part of spinosad as the present compound 1 and 4 parts of pyridalyl as the present compound 2 are added 5 parts of sodium dodecylbenzenesulfonate, 30 parts of bentonite and 60 parts of clay. The mixture is mixed and stirred thoroughly. Then, a proper amount of water is added to the mixture. The mixture is stirred, granulated with a granulator and then dried by ventilation to obtain a granule.

Formulation Example 12

5 parts of polyoxyethylene styrylphenyl ether sulfate, 20 parts of a 1% xanthan gum aqueous solution, 3 parts of a smectite mineral and 60 parts of water are mixed uniformly. To the mixture are added 2 parts of spinosad as the present compound 1 and 10 parts of pyridalyl as the present compound 2. The mixture is stirred thoroughly and then wet-milled with a sand mill to obtain a flowable formulation.

Formulation Example 13

0.02 part of spinosad as the present compound 1 and 0.1 part of pyridalyl as the present compound 2 are dissolved in 10 parts of acetone. The solution is uniformly mixed with 99.88 parts of a powdered solid animal feed (CE-2: powdered chow for breeding, manufactured by Clea Japan Inc.). Then, the mixture is air dried to remove acetone to obtain a poison bait.

Formulation Example 14

0.1 part of spinosad as the present compound 1 and 0.1 part of pyridalyl as the present compound 2 are dissolved in 5 parts of xylene and 5 parts of trichloroethane. The solution is mixed with 89.8 parts deodorized kerosene to obtain an oil solution.

The following Test Examples demonstrate that the present invention is effective in pest control. The theoretical value of an insecticidal (ovicidal) rate obtained by using a mixture of 2 kinds of active ingredients was calculated by the following formula:

$$E = X + Y - (X \times Y / 100),$$

which conforms to the Colby's formula.

X: Insecticidal rate (%) of the active ingredient A at M Ppm
Y: Insecticidal rate (%) of the active ingredient B at N ppm
E: Theoretical insecticidal rate (%) of combination use of the active ingredient A at M ppm and the active ingredient B at N ppm When an actual insecticidal (ovicidal) rate exceeds the theoretical value, it is determined that the used two active ingredients produce a synergetic effect.

Test Example 1

(1) 12 parts of spinetoram as the present compound 1, 35 parts of a carrier on which a polyoxyethylene alkyl ether sulfate ammonium salt and white carbon in a weight ratio of 1:1 were adsorbed, and 53 parts of water were mixed, and finely milled by a wet milling method to obtain a spinetoram formulation (hereinafter, referred to as the formulation A).

(2) A flowable formulation containing 10 parts of pyridalyl, which is the present compound 2, as the active ingredient (trade name: PLEO flowable, manufactured by Sumitomo Chemical Co., Ltd.) (hereinafter, referred to as the formulation B) was used.

(3) The formulation A was diluted with water to prepare a water dilution having an active ingredient concentration shown in Table 1. To the water dilution, 1/5,000 volume of a spreading agent (Sindain, manufactured by Sumitomo Chemical Takeda Agro Co., Ltd.) was added to prepare a test solution containing the present compound 1. The formulation B was diluted with water to prepare a water dilution having an active ingredient concentration shown in Table 1. To the water dilution, 1/5,000 volume of a spreading agent (Sindain, manufactured by Sumitomo Chemical Takeda Agro Co., Ltd.) was added to prepare a test solution containing the present compound 2.

A water dilution of the formulation A and a water dilution of the formulation B were mixed so that the respective active ingredients could reach concentrations shown in Table 1. To the mixture, 1/5,000 volume of a spreading agent (Sindain, manufactured by Sumitomo Chemical Takeda Agro Co., Ltd.) was added to prepare a test solution containing the present compound 1 and the present compound 2.

(4) A cabbage was planted in a pot and grown until the fourth leaf stage. The leaves of the cabbage were cut off one by one, and then immersed in the above-described test solution for 60 seconds. After air drying, the cabbage leaves were each placed in a cup with a filter paper spread on the bottom. Ten fourth-instar larvae of *Spodoptera litura* were released into each cup. After 2 days, the tested larvae were observed for life or death. An insecticidal rate was calculated and corrected according to the following formula.

Results are shown in Table 1.

Insecticidal rate (%)=100×($M_t$−$M_c$)/(100−$M_c$)

Mt: Worm death rate (%) in a section treated with a test compound

Mc: Worm death rate (%) in a section not treated with a test compound

The formulation B was diluted with water to prepare a water dilution having an active ingredient concentration shown in Table 2. To the water dilution, 1/5,000 volume of a spreading agent (Sindain, manufactured by Sumitomo Chemical Takeda Agro Co., Ltd.) was added to prepare a test solution containing the present compound 2.

A water dilution of the formulation A and a water dilution of the formulation B were mixed so that the respective active ingredients could reach concentrations shown in Table 2. To the mixture, 1/5,000 volume of a spreading agent (Sindain, manufactured by Sumitomo Chemical Takeda Agro Co., Ltd.) was added to prepare a test solution containing the present compound 1 and the present compound 2.

(2) A cabbage was planted in a pot and grown until the fourth leaf stage. The leaves of the cabbage were cut off one by one, and then immersed in the above-described test solution for 60 seconds. After air drying, the cabbage leaves were each placed in a cup with a filter paper spread on the bottom. Ten fourth-instar larvae of *Spodoptera litura* were released into each cup. After 2 days, the tested larvae were observed for life or death. An insecticidal rate was calculated and corrected according to the following formula.

Insecticidal rate (%)=100×($M_t$−$M_c$)/(100−$M_c$)

Mt: Worm death rate (%) in a section treated with a test compound

Mc: Worm death rate (%) in a section not treated with a test compound

TABLE 1

| Active ingredient in test solution | Active ingredient Concentration (ppm) | Theoretical value of insecticidal rate (%) | Found value of insecticidal rate (%) | Determination of synergetic effect |
|---|---|---|---|---|
| Spinetoram (present compound 1) + Pyridalyl (present compound 2) | 2.9 + 2.5 | 0 | 60.0 | Yes |
| | 0.73 + 2.5 | 0 | 50.0 | Yes |
| Spinetoram (present compound 1) | 2.9 | 0 | 0 | — |
| | 0.73 | 0 | 0 | — |
| Pyridalyl (present compound 2) | 2.5 | 0 | 0 | — |
| Untreated | — | | 0 | — |

Test Example 2

(1) The formulation A was diluted with water to prepare a water dilution having an active ingredient concentration shown in Table 2. To the water dilution, 1/5,000 volume of a spreading agent (Sindain, manufactured by Sumitomo Chemical Takeda Agro Co., Ltd.) was added to prepare a test solution containing the present compound 1.

TABLE 2

| Active ingredient in test solution | Active ingredient concentration (ppm) | Theoretical value of insecticidal rate (%) | Found value of insecticidal rate (%) | Determination of synergetic effect |
|---|---|---|---|---|
| Spinetoram (present compound 1) + Pyridalyl (present compound 2) | 0.25 + 2.5 | 16.7 | 80.0 | Yes |
| | 2.5 + 0.25 | 0 | 50.0 | Yes |
| Spinetoram (present compound 1) | 2.5 | — | 0 | — |
| | 0.25 | — | 0 | — |
| Pyridalyl (present compound 2) | 2.5 | — | 16.7 | — |
| | 0.25 | — | 0 | — |
| Untreated | — | — | 0 | — |

INDUSTRIAL APPLICABILITY

According to the present invention, it is possible to provide a pesticidal composition having an excellent controlling effect on pests, and so on.

The invention claimed is:

1. A pesticidal composition comprising:, a compound represented by the formula (I):

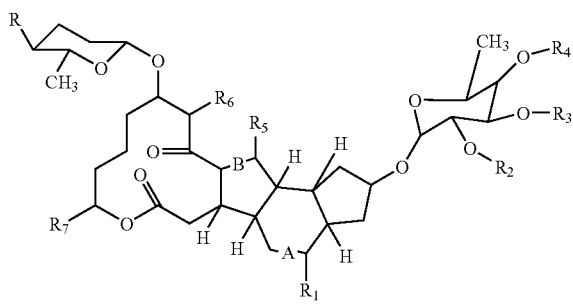

wherein A is a single bond or a double bond,
B is a double bond,
R is a group represented by the formula (II):

wherein $R_8$ and $R_9$ are methyl groups,
$R_1$ is a hydrogen atom or a methyl group,
$R_2$ is a methyl group,
$R_3$ is a methyl group or an ethyl group,
$R_4$ is a methyl group,
$R_5$ is a hydrogen atom,
$R_6$ is a methyl group, and
$R_7$ is an ethyl group; and
2,6-dichloro-4-(3,3-dichloroallyloxy)phenyl 3-[5-(trifluoromethyl)-2-pyridyloxy]propyl ether as active ingredients,
wherein a weight ratio of the compounds being from 10:1 to 1:10.

2. The composition according to claim 1, wherein $R_3$ is an ethyl group.

3. The composition according to claim 1, wherein the compound represented by the formula (I) is spinetoram.

4. A pest control method which comprises a step of applying an effective amount of a compound represented by the formula (I):

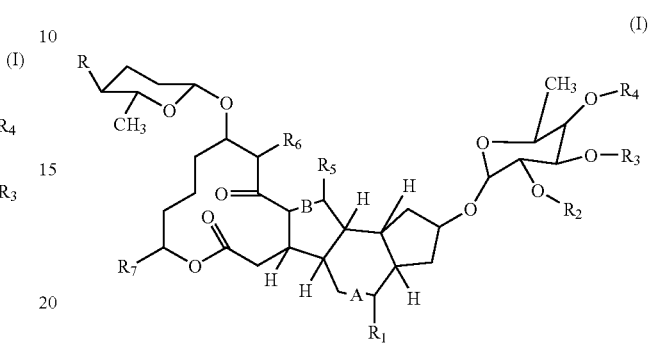

wherein A is a single bond or a double bond,
B is a double bond,
R is a group represented by the formula (II):

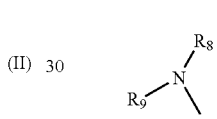

wherein $R_8$ and $R_9$ are methyl groups,
$R_1$ is a hydrogen atom or a methyl group,
$R_2$ is a methyl group,
$R_3$ is a methyl group or an ethyl group,
$R_4$ is a methyl group,
$R_5$ is a hydrogen atom,
$R_6$ is a methyl group, and
$R_7$ is an ethyl group; and
an effective amount of 2,6-dichloro-4-(3,3-dichloroallyloxy)phenyl 3-[5-(trifluoromethyl)-2-pyridyloxy]propyl ether to pests or a place where pests inhabit,
wherein a weight ratio of the compounds being from 10:1 to 1:10.

* * * * *